(12) United States Patent
Elger et al.

(10) Patent No.: US 7,507,725 B2
(45) Date of Patent: Mar. 24, 2009

(54) COMPOUNDS WITH SULPHONAMIDE GROUP AND PHARMACEUTICAL COMPOSITIONS CONTAINING THESE COMPOUNDS

(75) Inventors: Walter Elger, Berlin (DE); Alexander Hillisch, Jena (DE); Annemarie Hedden, Hamburg (DE); Sigfrid Schwarz, Jena (DE); Klaus Schollkopf, Berlin (DE)

(73) Assignee: Schering AG, Berlin (DE)

( * ) Notice: Subject to any disclaimer, the term of this patent is extended or adjusted under 35 U.S.C. 154(b) by 133 days.

(21) Appl. No.: 10/296,973

(22) PCT Filed: May 8, 2001

(86) PCT No.: PCT/EP01/05169

§ 371 (c)(1),
(2), (4) Date: Aug. 1, 2003

(87) PCT Pub. No.: WO01/91797

PCT Pub. Date: Dec. 6, 2001

(65) Prior Publication Data

US 2004/0014781 A1     Jan. 22, 2004

(30) Foreign Application Priority Data

May 31, 2000 (DE) .................. 100 27 887

(51) Int. Cl.
*A61K 31/56* (2006.01)
(52) U.S. Cl. .................. 514/182; 424/9.2; 424/1.65; 552/625; 552/617; 552/626
(58) Field of Classification Search ................ 424/1.11, 424/1.65, 9.1, 9.2; 514/176, 182; 552/617, 552/625
See application file for complete search history.

(56) References Cited

U.S. PATENT DOCUMENTS

| | | | |
|---|---|---|---|
| 4,244,950 A | 1/1981 | De Ritter et al. | |
| 4,513,006 A | 4/1985 | Maryanoff et al. | |
| 4,659,516 A * | 4/1987 | Bowler et al. | 514/144 |
| 4,792,569 A | 12/1988 | Maryanoff et al. | |
| 5,001,234 A | 3/1991 | Bundy et al. | |
| 5,025,031 A | 6/1991 | Lo et al. | |
| 5,116,828 A | 5/1992 | Miura et al. | |
| 5,705,495 A * | 1/1998 | Schwarz et al. | 514/182 |
| 5,866,603 A | 2/1999 | Li et al. | |
| 6,339,079 B1 | 1/2002 | Kasch et al. | |
| 6,355,666 B1 | 3/2002 | Lai et al. | |
| 6,436,917 B1 * | 8/2002 | Droescher et al. | 514/176 |
| 6,583,130 B1 | 6/2003 | Schwarz | |
| 6,713,487 B2 | 3/2004 | Yu et al. | |
| 6,841,548 B2 | 1/2005 | Schwarz | |
| 6,956,031 B2 | 10/2005 | Hillisch | |
| 6,958,327 B1 * | 10/2005 | Hillisch et al. | 514/182 |

| | | |
|---|---|---|
| 2004/0014781 A1 | 1/2004 | Elger |
| 2004/0087565 A1 | 5/2004 | Kosemund et al. |
| 2005/0277625 A1 | 12/2005 | Wyrwa et al. |
| 2005/0288267 A1 | 12/2005 | Wyrwa et al. |

FOREIGN PATENT DOCUMENTS

| | | |
|---|---|---|
| DE | 12 03 042 | 10/1965 |
| DE | 42 36 237 A1 | 4/1994 |
| DE | 19712488 A1 | 10/1998 |
| EP | 0 003 383 A2 | 8/1979 |
| EP | 0 424 954 A | 5/1991 |
| WO | WO93/05064 | 3/1993 |
| WO | WO94/14827 | 7/1994 |
| WO | WO94/26702 | 11/1994 |
| WO | WO96/05216 | 2/1996 |
| WO | WO97/14712 | 4/1997 |
| WO | WO 00/06475 | 2/2000 |
| WO | WO 01/51055 | 7/2001 |
| WO | WO 01/77139 A1 | 10/2001 |
| WO | WO 01/91797 A | 12/2001 |
| WO | WO 03/104253 A2 | 12/2003 |

(Continued)

OTHER PUBLICATIONS

Barth A et al.: "Influence Of Subchronic Administration Of Oestradiol, Ethinyloestradiol and Oestradiol Sulphamate On Bile Flow, Bile Acid Excretion, And Liver And Biliary Glutathione Status in Rats", Archives of Toxicology, Springer Verlag, DE, vol. 71, No. 7, 1997, pp. 443-449, XP000986430, ISSN 0340-5761.

(Continued)

*Primary Examiner*—D. L. Jones
(74) *Attorney, Agent, or Firm*—Millen, White, Zelano & Branigan, P.C.

(57) ABSTRACT

The invention relates to compounds which, acting as a prodrug and/or support, enable an active agent to be taken up by the erythrocytes and/or an active agent to bind to the erythrocytes. The uptake of these compounds by and/or the binding thereof to the erythrocytes is made possible by a group of formula —$SO_2NR_1R_2$, wherein $R_1$ and $R_2$, independently of each other, mean a hydrogen atom, an acyl group, an alkyl group, a cycloalkyl group, an aryl group, a cyano group or a hydroxy group. The inventive prodrugs enable active agents such as endogenic substances, natural substances and synthetic substances with therapeutically useful properties which have a high "first path" effect, to be administered orally effectively or significantly improve the oral activity thereof.

18 Claims, 5 Drawing Sheets

FOREIGN PATENT DOCUMENTS

| | | |
|---|---|---|
| WO | WO 2005/051401 A2 | 6/2005 |
| WO | WO 2005/113574 A1 | 12/2005 |
| WO | WO 2005/113575 A | 12/2005 |
| WO | WO 2005/113576 A | 12/2005 |
| WO | WO 2006/108879 A | 10/2006 |

OTHER PUBLICATIONS

Elger W et al.: "Sulfamates Of Various Estrogens Are Prodrugs With Increased Systemic And Reduced Hepatic Estrogenicity At Oral Application", Journal of Steroid Biochemistry and Molecular Biology, Elsevier Science Ltd., Oxford, GB, vol. 55, No. 3-4, 1995, pp. 395-403, XP000618892, ISSN 0960-0760.

Maryanoff B E et al.: "Anticonvulsant Sugar Sulfamates. Potent Cyclic Sulfate And Cyclic Sulfite Analogues Of Topiramate", Bioorganic & Medicinal Chemistry Letters, Oxford, GB, vol. 3, No. 12, 1993, pp. 2653-2656, XP000914306, ISSN 0960-894X.

"Synthesis of estrogen sulfamates: Compounds with a novel endocrinological profile", Sigfrid Schwarz et al., Steroids, 1996, vol. 61, Dec. pp. 710-717.

Jahrgang 30, Hefte 1-12—1975—Die Pharmazie, Steroide, S. Schwarz et al., pp. 17-21.

Chemische Berichte, Rolf Appel und Werner Senkpiel, pp. 1102-1105, 1959.

Annalen Der Chemic, Herstellung and Reaktionen von N-Monoalkyl-amidosulfonylchloriden, von Gunther Weiβ et al., pp. 40-51, 1969.

"X-ray Crystal Structure and Mechanism of Action of Oestrone 3-O-Sulphamate, a Synthetic Active Site-directed Inhibitor of Oestrone Sulphatase", Gary J. Williams et al., Pharmaceutical Sciences 1996, pp. 11-16.

"Development of an Oral Formulation for Oestrone 3-O-Sulphamate, a Potent Sulphatase Inhibitor", Ulrike G. Sahm et al., Pharmaceutical Sciences 1996, pp. 17-20.

17β-Hydroxy-11α-(3'-sulfanylpropyl)oxy-estra-1,3,5(10)-trien-3-yl sulfamate—a novel hapten structure: Toward the development of a specific enzyme immunoassay (EIA) for estra-1,3,5(10)-triene-3-yl sulfamates, Steroids 64 (1999), pp. 460-471.

US-2004-0102630 CDK-inhibitory pyrimidines, their production and use as pharmaceutical agents.

Guide-0001; U.S. Appl. No. 10/271,165 filed Aug. 13, 2002.

Guide-0005; U.S. Appl. No. 10/296,973 filed Aug. 1, 2003.

J. Med Chem. Jun. 23, 1995;38(13):2286-91 - Secondary interactions significantly removed from the sulfonamide binding pocket of carbonic anhydrase II influence inhibitor binding constants - Boriack PA, Christianson DW, Kingery-Wood J., Whitesides GM.

Blood Carbonic Anhydrase Activity In Anemia, With A Note On Polycythemia Vera, H.D. Lewis et al., pp. 442-454. (date not available).

Enzymatic Conjugation of Erythrocyte Glutathione With 1-Chloro-2,4-Dinitrobenzene: The Fate of Glutathione Conjugate in Erythrocytes and the Effect of Glutathione Depletion on Hemoglobin, Yogesh C. Awasthi et al., pp. 733-738. (date not available).

J.Med Chem. Aug. 7, 1992;35(16):3027-33 - Thieno[2,3-b]furan-2-sulfonamides as topical carbonic anhydrase inhibitors - Hartman GD et al.

J Biol Chem. Dec. 15, 1993;268(35):26233-9 - A new class carbonic anhydrase inhibitor - Maren TH et al.

Int J Biol Macromol. Apr. 1993;15(2):97-100 - Refined structure of the aminobenzolamide complex of human carbonic anhydrase II at 1.9 A and sulphonamide modeling of bovine carbonic anhydrase III - Vidgren J et al.

J Med Chem. Jan. 21, 1994;37(2):240-7 - 3-substituted thieno[2,3-b][1,4]thiazine-6-sulfonamides. A novel class of topically active carbonic anhydrase inhibitors - Hunt CA et al.

Mol Pharmacol. Sep. 1995;48(3):486-91 - The effect of temperature on the binding of sulfonamides to carbonic anhydrase isoenzymes I, II, and IV - Conroy CW et al.

Biorg Med Chem. Mar. 1997;5(3):515-8 - Synthesis and investigation of inhibition effects of new carbonic anhydrase inhibitors - Arslan O. Kufrevioglu et al.

Protein Sci. Dec. 1998;7(12):2483-9 - Structual analysis of inhibitor binding to human carbonic anhydrase II - Boriack-Sjodin et al.

Bioorg Med Chem. Nov. 1999;7(11):2397-406 - Carbonic anhydrase inhibitors: synthesis of water-soluble, topically effective intraocular pressure lowering aromatic-heterocyclic sulfonamides containing 8-quinoline-sulfonyl moieties: is the tail more important than the ring?- Borras J. et al.

Bioorg Med Chem. May 2000;8(5):957-75 - 2H-Thieno[3,2-e]- and [2,3-e]-1,2-thiazine-6-sulfonamide 1,1-dioxides as ocular hypotensive agents: synthesis, carbonic anhydrase inhibition and evaluation in the rabbit - Chen HH et al.

Brinzolamide, Ophthalmic Suspension 1%, Azopt - Summary Basis Of Approval Equivalent, Alcon Laboratories, Inc., pp. 1-23. (date not available).

Azopt (brinzolamide ophthaimic suspension) 1%, Alcon Laboratories, Inc., pp. 1-3. (date not available).

Annex I Summary of Product Characteristics pp. 1-22. (date not available).

U.S. Appl. No. 11/605,482.

U.S. Appl. No. 11/605,473.

Office Action dated Mar. 18, 2008 in U.S. Appl. No. 11/605,473.

Chandler, Surinder K. et al., "The Role of Steroid Sulphatase in Regulating the Oestrogenicity of Estrogen Sulphamates," Biochemical and Biophysical Research Communications, 2004, pp. 217-222, vol. 322, Elsevier, Inc.

Elger, W. et al., "Estrogen Sulfamates: a New Approach to Oral Estrogen Therapy," Reprod. Fertil. Dev., 2001, pp. 297-305, vol. 13, CSIRO Publishing, Australia.

Purohit, A. et al., "Steriod Sulphatase Inhibitors for Breast Cancer Therapy," Journal of Steriod Biochemistry & Molecular Biology, 2003, pp. 423-432, vol. 86, Elsevier Ltd.

Williams, J. et al., "The Oral Administration of Polysorbate 80 to the Immature Female Rat Does Not Increase Uterine Weight," Toxicology Letters, 1997, pp. 19-24, vol. 91, Elsevier Science Ireland Ltd.

Claude A. Quesnelle et al., "Sordaricin Antifungal Agents," Bioorganic and Medicinal Chemistry Letters, Feb. 10, 2003, vol. 13, No. 3, pp. 519-524, XP002432733, ISSN:0960-894X.

Carolyn H. Kruse et al., "Synthesis and Evaluation of Multisubstrate Inhibitors of an Oncogene-Encoded Tyrosine-Specific Protein Kinase," J. Med. Chem., Sep. 1998, vol. 31, No. 9, pp. 1762-1767, XP002432734, ISSN: 0022-2623.

Sally-Ann Poulsen et al., "Synthesis and Structure-activity relationships of novel benzene sulfonamides with potent binding affinity for bovine carbonic anhydrase II," Oct. 6, 2005, pp. 5429-5433, XP005136456, ISSN: 0960-894X.

Takuo Aoyama et al., "Synthesis and Structure-Activity Study of Protease Inhibitors," Chemical and Pharmaceutical Bulletin, Pharmaceutical Society of Japan, 1985, vol. 33 No. 4, pp. 1458-1471, XP002110067, ISSN: 0009-2363.

Gomes J R B et al., "Gas-phase acidity of sulfonamides: implications for reactivity and prodrug design", Tetrahedron, Mar. 7, 2005, 2705-2712, vol. 61, Nbr. 10, Elsevier Science Publishers, Amsterdam.

International Search Report for related international application PCT/EP2006/011727, filed Nov. 27, 2006; Search conducted Mar. 27, 2007.

U.S. Appl. No. 11/605,472 (year not provided).

U.S. Appl. No. 11/604,891 (year not provided).

U.S. Appl. No. 11/134,618 (year not provided).

U.S. Appl. No. 11/133,431 (year not provided).

Office Action dated Dec. 27, 2007 in U.S. Appl. No. 11/605,472.

Office Action dated Feb. 29, 2008 in U.S. Appl. No. 11/604,891.

Office Action dated Feb. 5, 2008 in U.S. Appl. No. 11/134,618.

* cited by examiner

COMPOUNDS WITH SULPHONAMIDE GROUP AND PHARMACEUTICAL COMPOSITIONS CONTAINING THESE COMPOUNDS

This invention relates to compounds that as prodrugs and/or vehicles make it possible to take up an active ingredient into erythrocytes and/or to bind an active ingredient to erythrocytes.

The purpose of this invention is to make active ingredients, such as endogenous substances, natural substances and synthetic substances with therapeutically valuable properties and with a high "first pass" effect, available orally to a reasonable extent or to improve them decisively relative to oral activity.

This purpose is achieved by an-optionally substituted sulfonamide group being incorporated in the active ingredient, i.e. as an "anchor," that makes possible the uptake into erythrocytes or the binding to erythrocytes.

This means that this invention relates to compounds that as prodrugs and/or vehicles make it possible to take up an active ingredient into erythrocytes and/or to bind an active ingredient to erythrocytes, whereby the uptake of the compounds into erythrocytes and/or the binding of the compounds to erythrocytes is made possible by a group

—SO$_2$NR$^1$R$^2$ whereby R$^1$ and R$^2$, independently of one another, mean a hydrogen atom, an acyl group, an alkyl group, a cycloalkyl group, an aryl group, a cyano group or a hydroxy group.

One of radicals R$^1$ and R$^2$ preferably means a hydrogen atom; both radicals R$^1$ and R$^2$ especially preferably mean a hydrogen atom.

The N-mono-substituted compounds or N,N-disubstituted compounds of the invention can have one or two N-alkyl, N-alkenyl, N-cycloalkyl, N-acyl or N-aryl substituents, which in each case preferably have up to 10 carbon atoms. R$^1$ and/or R$^2$ mean in particular an alkyl or acyl group with 1 to 6 carbon atoms. Examples are a methyl, ethyl, propyl or isopropyl group or the corresponding acyl derivatives. Examples of an aryl group are a phenyl group or a tolyl group. Examples of a cycloalkyl group are a cyclopentyl group or a cyclohexyl group.

Figure 1:
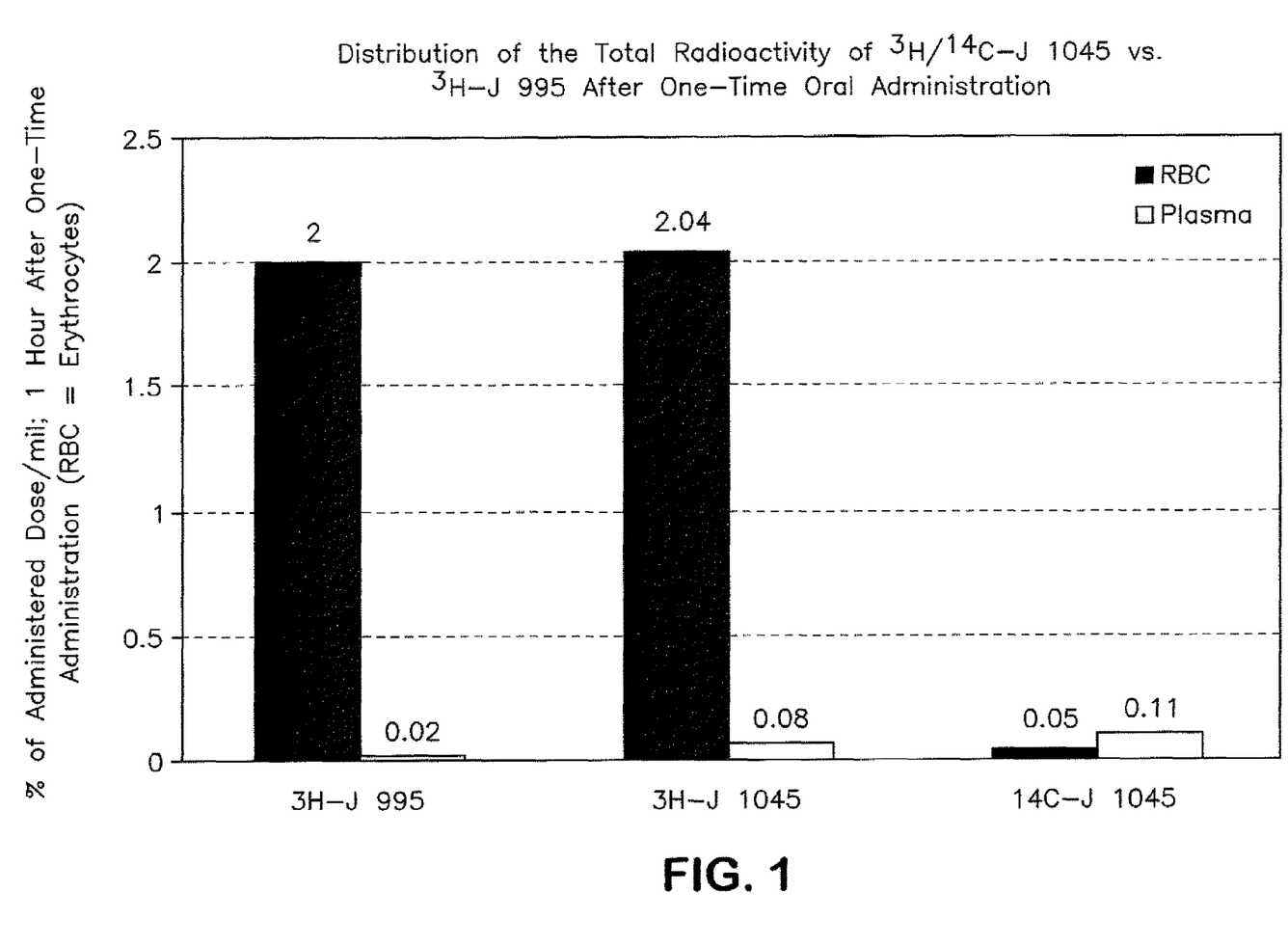
FIG. 1 shows the distribution of the total radioactivity of $^3$H/$^{14}$C-J 1045 vs. $^3$H-J 995 after a one-time oral administration.

There are indications that in oral administration, both radicals R$^1$ and R$^2$, if they are different from a hydrogen atom, are cleaved off and are replaced by a hydrogen atom, so that in this case, not the group —SO$_2$NR$^1$R$^2$, but rather the group —SO$_2$NH$_2$ is provided for the uptake into erythrocytes or binding to erythrocytes. FIG. 1 is a diagram that shows the different activity distribution for tritium around $^{14}$C on erythrocytes and plasma after oral administration of 17β-hydroxyestra-1,3,5(10)-trien-3-yl-(N-acetyl)sulfamate (J1045, $^{14}$C-labeled acyl substituent and $^3$H-labeled steroid skeleton). As can be seen from the figure, the $^{14}$C-labeled acyl substituent of the sulfamate radical is no longer present in the-blood after oral administration. The data also confirm that substances according to the invention are enriched in the erythrocyte compartment relative to the plasma.

The sulfonamide group that is preferred according to the invention can thus also be formed first in the body from N-monosubstituted or N,N-disubstituted sulfonamide groups, for example N-acylsulfonamides.

According to the invention, a prodrug (pro-pharmaceutical agent) is defined as a pharmaceutical agent that is also largely inactive biologically and that is reacted into the actual active ingredient only once it enters the body. In addition to the actions of the active ingredient, the prodrug can also have additional pharmacological actions. If these actions are predominantly or fully therapy-relevant actions, the compounds according to the invention are to be considered in boundary cases also as active ingredients and not just as prodrugs ("vehicles").

The uptake of compounds into erythrocytes or the binding of compounds to erythrocytes is carried out via hemoglobin, membrane proteins and/or carboanhydrase, i.e., carboanhydrase I (hCAI) and II (hCAII).

A depot of the active ingredient is formed in erythrocytes by the uptake of compounds into erythrocytes and/or by the binding of the compounds to erythrocytes, whereby an essential portion of the active ingredient in the body is present in erythrocytes.

According to the invention, the term "depot formation" is defined in that the compound (or the active ingredient) is enriched in the erythrocytes by a factor 10 to 1000, preferably 20 to 1000, especially preferably 30 to 1000, above the plasma level, whereby the factor is determined after separation from erythrocytes and plasma by centrifuging and determining the concentration of the substance according to the invention in erythrocytes and plasma. For estradiol sulfamate (J995), it was found that the above-mentioned factor is 98:2 at any time.

Basically, the compounds are compounds that exert their action in the erythrocytes. The compounds and/or the active ingredient contained in the compounds in this case preferably prevent the parasitic attack of the erythrocytes that is an essential aspect of the disease, for example, in malaria.

The compounds preferably have the following structure:

Active-ingredient-[Spacer]n-SO$_2$NR$^1$R$^2$ whereby n means a number 0 or 1 R$^1$ and R$^2$ have the meaning given above, and the active ingredient in its free form has at least one functional group, whereby preferably at least one of radicals R$^1$ and R$^2$ means a hydrogen atom and especially preferably both mean a hydrogen atom.

If the compounds act as a prodrug, the therapeutically desirable action is obtained by release, especially hydrolytic cleavage, of the active ingredient that is contained in the product and/or its metabolites. For J995, it was found that this compound is stable in the erythrocytes, and the release of the active ingredient from the prodrug is carried out only in the plasma or in tissues.

If n is 0, the functional group is preferably a group —OH, which forms a group —O—SO$_2$NH$_2$ with the group —SO$_2$NH$_2$, a group =O, which is converted into a group =N—OH or =N—NH$_2$ and forms a group =N—O—SO$_2$NH$_2$ or =N—NH—SO$_2$NH$_2$ with the group —SO$_2$NH$_2$, a group —NHR, which forms a group —NR—SO$_2$NH$_2$ with the group —SO$_2$NH$_2$, whereby R is a hydrogen atom or an alkyl group, preferably with 1 to 4 carbon atoms, or NR is part of a heterocyclic ring system, as is the case, for example, in melatonin or some of the cited anti-malaria agents, or a group —SH, which forms a group —S—SO$_2$NH$_2$ with the group —SO$_2$NH$_2$.

If n is 1, the functional group is preferably a group —COOH or a group that is derived from this group, such as an ester group, which together with the spacer and with the group —SO$_2$NH$_2$ forms a group —C(O)-spacer-SO$_2$NH$_2$, whereby the spacer in this case is a group-A-B—(O)$_s$, whereby s is a number 0 or 1, A stands for S, O or NR$^3$, whereby R$^3$ is a hydrogen atom, an alkyl group, preferably with 1 to 4 carbon atoms, or an acyl group, preferably with 1 to 4 carbon atoms, and B is selected from an alkylene group, an arylene group, an alkylene arylene group or an alkylene arylenealkylene group, which are optionally substituted.

If n is 1, the functional group is also preferably a group —YH, which together with the spacer and with the group —$SO_2NH_2$ forms a group —Y-spacer-$SO_2NH_2$, whereby Y stands for S, O or $NR^4$, whereby $R^4$ is a hydrogen atom, an acyl group, preferably with 1 to 4 carbon atoms, or an alkyl group, preferably with 1 to 4 carbon atoms, or $NR^4$ is part of a heterocyclic ring system, whereby the spacer is a group whereby t and p are a number 0 or 1, and E is selected from an alkylene group, an arylene group, an alkylene arylene group or an alkylene arylenealkylene group, which optionally are substituted, or, whereby the spacer means a group whereby n and q are a number 0 or 1, $R^5$ and $R^6$, independently of one another, mean a hydrogen atom or an alkyl group, preferably with 1 to 4 carbon atoms, and D means an arylene group, especially a phenylene group, or whereby the spacer means a group whereby r and v are a number 0 or 1, and m means a number from 1 to 15.

The structure of the compounds according to the invention was explained for reasons of simplicity based on the group —$SO_2NH_2$. What is stated above for the group —$SO_2NH_2$ correspondingly applies to the group —$SO_2NR^1R^2$.

The active ingredient can basically be any active ingredient that has at least one of the above-mentioned functional groups and is bonded by means of the latter, optionally via a spacer, to the group —$SO_2NR^1R^2$.

The active ingredient is preferably selected from androgens, anabolic agents, antiandrogens, estrogens, gestagens, glucocorticoids, amoebicides, anti-diuretic agents, antigonatropines, ulcer therapeutic agents, neuropharmaceutical agents, dopamine receptor antagonists, dopamine, apomorphine, melatonin and peptides, such as GnRH (gonatropin releasing hormones) and other hypothalamic, regulatory active peptides.

The active ingredient is preferably an androgen, such as testosterone, whereby the functional group is the 17-hydroxy group or the 3-carbonyl group of the androgen.

The active ingredient is preferably an estrogen, such as estradiol, estriol or estrone, whereby the functional group is a 3-, 16- or 17-hydroxy group or 17-carbonyl group.

The active ingredient is preferably a gestagen, such as norethisterone, dienogest, drospirenone or levonorgestrel, whereby the functional group is a 17-hydroxy group or a 3-carbonyl group.

The active ingredient is especially preferably an anti-malaria agent, such as arteether, artemether, artesunate, chloroquine, pamaquine, primaquine, pyrethamine, mefloquine, proguanil, cinchonidine, cinchonine, hydroxychloroquine, pamaquine, primaquine, pyrimethamine as well as quinine or a quinine derivative, such as quinine-bisulfate, quinine-carbonate, quinine-dihydrobromide, quinine-dihydrochloride, quinine-ethylcarbonate, quinine-formate, quinine-gluconate, quinine-hydroiodide, quinine-hydrochloride, quinine-salicylate or quinine-sulfate.

The compounds (prodrugs) impart to the pharmaceutical substances, in addition to their pharmodynamic properties, the ability to accumulate in the red blood cells (erythrocytes). This results in the following therapy-relevant properties or advantages:

1. Endogenous substances, natural substances and synthetic substances with therapeutically valuable properties with a high "first pass" effect are available orally to a reasonable extent only by the described modification or are decisively improved relative to oral activity. The uptake of the substances according to the invention into the erythrocytes prevents their extraction from the blood during the (first) passage through the liver and thus their metabolism and excretion.
2. The modification according to the invention results in a reduction of undesirable effects of these substances in the liver in comparison to the unsubstituted starting substance.
3. The concentration in erythrocytes by a multiple of the plasma concentration can be used especially if the action in the erythrocyte is the purpose of the therapy. This is the case in parasitic attack of erythrocytes, for example in malaria.
4. Almost all endogenous hormones, transmitter substances and many active ingredients are limited in their therapeutic applicability by metabolism that occurs too quickly and elimination. The modification according to the invention results in a decisive extension of the dwell time of the active substance in the organism via a depot that is produced in the erythrocytes. The occurrence of very high levels in the plasma shortly after the administration is avoided. This is an advantage, especially in the case of all substances that exert actions in the central and peripheral nervous system.
5. This invention describes, i.a., prodrugs. The prodrugs are bonded to erythrocytes. The therapeutically desired action is carried out by the (hydrolytic) release of the acid from its prodrug.

The compounds according to the invention can be used in principle in connection with transcutaneous administration, inhalation or injection. The therapy-relevant properties or advantages of the prodrugs according to the invention are used in particular in oral administration, however.

By nature, the success of a pharmacotherapy depends decisively on the pharmacodynamic and pharmacokinetic properties of the respective therapeutic agents. In addition, the form of dispensing the pharmaceutical agent is decisive for the success of the therapy. The latter has a decisive influence on the applicability of a principle of action by physician or patient and the "compliance" of the patient. It can be considered as certain that an oral therapy form ensures a better "compliance" than any other form of administration.

One reason for the high acceptance of the oral administration is for one thing the simplicity of the administration and the good controllability of a therapy. Another essential reason for the excellent "compliance" of the oral administration should be related to the fact that we are accustomed to taking food, liquid and stimulants by mouth. Other administration processes can be regarded as traumatic or unnatural, however, and are thus discouraged in terms of longer-lasting forms of therapy.

FUNCTIONAL GROUPS

The functional group can basically be any group with which a group —SO$_2$NR$^1$R$^2$ can be introduced, optionally by means of a spacer.

As already stated above, the compounds according to the invention preferably have the following structure:

Active ingredient-[Spacer]n-SO$_2$NH$_2$ whereby n means a number 0 or 1, and the active ingredient in the free form has a functional group.

If n is 0, the functional group is preferably
  a group —OH, which forms a group —O—SO$_2$NH$_2$ with the group —SO$_2$NH$_2$,
  a group =O, which is converted into a group =N—OH or =N—NH$_2$ and forms a group =N—O—SO$_2$NH$_2$ or =N—NH—SO$_2$NH$_2$ with the group —SO$_2$NH$_2$,
  a group —NHR, which forms a group —NR—SO$_2$NH$_2$ with the group —SO$_2$NH$_2$, whereby R is a hydrogen atom or an alkyl group, preferably with 1 to 4 carbon atoms, or NR is part of a heterocyclic ring system, or
  a group —SH, which forms a group —S—SO$_2$NH$_2$ with the group —SO$_2$NH$_2$.

If n is 1, the functional group can be a group —COOH (or a group derived therefrom, such as an ester group), which together with the spacer and with the group SO$_2$NH$_2$ forms a group —C(O)-spacer-SO$_2$NH$_2$.

If n is 1, the functional group in addition can be a group —YH, which together with the spacer and with the group —SO$_2$NH$_2$ forms a group —Y-spacer-SO$_2$NH$_2$, whereby Y means S, O or NR$^4$, whereby R$^4$ is a hydrogen atom or an alkyl group, preferably with 1 to 4 carbon atoms, or NR$^4$ is part of a heterocyclic ring system.

Active Ingredients

The active ingredient can basically be any active ingredient that has a functional group and can be bonded via the latter, optionally via a spacer, to the group —SO$_2$NR$^1$R$^2$.

The principle according to the invention is suitable especially for endogenous substances, natural substances and synthetic substances with therapeutically valuable properties that have a high "first pass" effect. The latter are actually available orally to a reasonable extent only by the described modification or are decisively improved relative to oral activity.

In particular, the principle according to the invention for the following active ingredient classes or active ingredients is suitable:

Hormones that can be described by the skeleton that is cited below and have at least one functional group, preferably one of the above-mentioned functional groups, in the molecule, to which the group SO$_2$NR$^1$R$^2$ can be coupled.

Anabolic agents or androgens that have a group HO— or C=O preferably in 3- or 17-position, whereby examples of anabolic agents are nandrolone methenolone, and trenbolone (functional group: C=O or OH) as well as prasterone (functional group: C=O or OH) and examples of androgens are mesterolone, dehydroepiandrosterone and testosterone (functional group: C=O or OH).

Antiandrogens, such as Casodex® (functional group: OH) and cyproterone or cyproterone-acetate (functional group: OH, C=O).

Gestagens that have a group HO— or C=O preferably in 3- or 17-position, whereby example are dienogest, levonorgestrel, hydroxyprogesterone, norethisterone as well as gestagens that are derived from ethinylestradiol or 17α-hydroxyprogesterone or 19-nortestosterone (functional group: 17-OH, 3-C=O), and drospirenone (functional group: C=O).

Estrogens that preferably have a 3-, 16- or 17-hydroxy group and/or 17-carbonyl group as a functional group, such as estradiol, estriol or estrone (functional group: OH group, C=O group).

Glucocorticoids, such as cortisone, dexamethasone and prednisolone (functional group: OH, C=O).

Amoebicides, such as metronidazole, chlorotetracycline, oxytetracycline, demecycline, and tetracycline (functional group: OH) as well as chlorochin (functional group: NH).

Antidiuretic agents, such as vasopressin, desmopresin, felypressin, lypressin, ornipressin and terlipressin (functional group: NH).

Antigonadotropins, such as danazol and paroxypropione (functional group: OH).

Ulcer therapeutic agents, such as the prostaglandin misoprostol (functional group: OH).

Dopamine receptor agonists, such as dopexamine, lisuride and pergolide (functional group: OH and/or NH) as well as dopamine (functional group: OH).

Neuropharmaceutical agents and agents against cancer.

Peptides, such as GnRH and other hypothalamic, regulatory active peptides.

Antimalaria agents, such as arteether, artemether, artemisinine, artesunate (functional group: OH, C=O), chloroquine, pamaquine, primaquine, pyrethamine (functional group: NH), mefloquine (functional group: NH, OH), proguanil (functional group: C=NH), cinchonidine, cinchonine (functional group: OH), hydroxychloroquine (functional group: OH, NH), pamaquine, primaquine, pyrimethamine (functional group: NH) as well as quinine and quinine derivatives, such as quinine-bisulfate, quinine-carbonate, quinine-dihydrobromide, quinine-dihydrochloride, quinine-ethylcarbonate, quinine-formate, quinine-gluconate, quinine-hydroiodide, quinine-hydrochloride, quinine-salicylate and quinine-sulfate (functional group: OH).

Spacer

According to the invention, the term "spacer" is defined as a carbon chain and/or one or more aryl groups between the group —SO$_2$NHR and the functional group of the active ingredient.

Because of the bio-availability and the transport through the membranes, the compounds according to the invention preferably have a molecular weight below 600.

If the functional group is a group —COOH, the spacer is preferably a group -A-B—(O)$_s$—, whereby s is a number 0 or 1, A stands for S, O or NR$^3$, whereby R$^3$ is a hydrogen atom, an alkyl group, preferably with 1 to 4 carbon atoms, or an acyl group, preferably with 1 to 4 carbon atoms, and B is selected from an alkylene group, an arylene group, an alkylene arylene group or an alkylene arylenealkylene group, which are optionally substituted.

If the functional group is a group —YH, the spacer is preferably a group whereby t and p are a number 0 or 1, and E is selected from an alkylene group, an arylene group, an alkylene arylene group or an alkylene arylenealkylene group, which optionally are substituted, or a group whereby q and n are a number 0 or 1, R$^5$ and R$^6$, independently of one another, mean a hydrogen atom or an alkyl group, preferably with 1 to 4 carbon atoms, and D means an arylene group, especially a phenylene group, which optionally can be substituted, or a group whereby r and v are a number 0 or 1, and m means a number from 1 to 15.

Alkylene group is defined according to the invention as a branched or unbranched alkylene group with 1 (or 2) to 20, preferably 1 (or 2) to 10 carbon atoms, which optionally can be substituted. The substituent or substituents can be selected from C$_{1-4}$-alkyl groups, C$_{1-4}$-alkoxy groups, C$_{1-4}$-acyl groups, halogen atoms, such as a fluorine, chlorine, bromine or iodine atom, a hydroxy group or a carbonyl group. Examples of an alkylene group are methylene, ethylene, propylene, butylene, pentylene, hexylene, heptylene, octylene, nonylene, decylene and undecylene groups, which can be branched or unbranched and optionally can be substituted with one or more of the above-mentioned substituents.

The term alkylene group according to the invention also comprises a branched or unbranched alkenylene group and an alkinylene group with 2 (or 3) to 20, preferably 2 (or 3) to 10 carbon atoms, which optionally can be substituted with the above-mentioned substituents. Examples of an alkenylene or alkinylene group are derived from the examples that are provided above for the alkylene group, whereby one or more double bonds or triple bonds (up to 4) can be present.

The term alkylene group according to the invention also comprises a cycloalkylene group with 5 to 20, preferably 5 to 10 carbon atoms, which optionally can be substituted. Examples are a cyclopentylene or cyclohexylene group.

An arylene group is defined according to the invention as an arylene group with 6 to 20 carbon atoms, which optionally can be substituted. The substituent or substituents can be selected from halogen atoms, such as a fluorine, chlorine, bromine or iodine atom, a hydroxy group, an amino group, a nitro group, a C$_{1-4}$ alkoxy group, an acyl group, or a C$_{1-4}$-alkyl group. Examples of an arylene group are a phenylene group, a halophenylene group, a hydroxyphenylene group or a naphthylene group, whereby a phenylene group is preferred.

An arylene group is also defined according to the invention as a heteroarylene group with 5 to 20 carbon atoms, whereby 1 to 3 carbon atoms can be replaced by a sulfur atom, an oxygen atom or a nitrogen atom. Examples of a heteroarylene group are derived from a pyridine, furan, thiophene, pyrrole, imidazole, pyrazine, pyrimidine or pyridazine ring.

An alkylene arylene group is defined according to the invention as an unbranched or branched alkylene group with 1 to 14 carbon atoms, which is associated with an arylene group with 6 to 19 carbon atoms. For both radicals, the definitions already provided above for the alkylene group or arylene group hold true with the exception of the number of carbon atoms. Examples of an alkylene arylene group are a benzylidene group or a substituted benzylidene group, in which one or both hydrogen atoms of the methylene group are exchanged for a C$_{1-4}$-alkyl group.

An alkylene arylenealkylene group is defined according to the invention as a branched or unbranched alkylene group with 1 to 13 carbon atoms, which is associated with an arylene group with 6 to 18 carbon atoms, which in turn is associated with an unbranched or branched alkylene group with 1 to 13 carbon atoms. For both types of groups, the definitions already provided above for the alkylene group or arylene group hold true with the exception of the number of carbon atoms. Preferred is a group whereby f and i are a number 0 or 1, -g and h mean a number from 1 to 5, and R$^7$ and R$^8$, independently of one another, mean a hydrogen atom or a C$_{1-4}$-alkyl group.

Examples of an alkyl group with 1 to 4 carbon atoms are a methyl, ethyl, propyl, iso-propyl, butyl- or tert-butyl group.

Examples of an alkoxy group with 1 to 4 carbon atoms are a methoxy, ethoxy, propoxy, isopropoxy and tert-butyloxy group.

Examples of a C$_{1-4}$-acyl group are an acetyl group, propionyl group or butyryl group.

Halogen atom is defined in this invention as a fluorine, chlorine, bromine or iodine atom.

Pharmaceutical Compositions

Subjects of the invention are also pharmaceutical compositions that contain at least one compound according to the invention together with pharmaceutically compatible adjuvants and/or vehicles.

Pharmaceutical agents of this invention are produced with commonly used solid or liquid vehicles and/or diluents and the adjuvants that are generally commonly used according to the desired type of administration in a suitable dosage and in a way that is known in the art. In the preferred oral dispensing form, tablets, film tablets, coated tablets, capsules, pills, powders, solutions or suspensions are also preferably prepared as depot forms.

Pharmaceutical forms as tablets can be obtained, for example, by mixing active ingredient with known adjuvants, such as dextrose, sugar, sorbitol, mannitol, polyvinyl pyrrolidone, explosives such as corn starch or alginic acid, binders such as starch or gelatin, lubricants such as magnesium stearate or talc. The tablets can also consist of multiple layers or can have a break-line.

In addition, coated tablets can be prepared by coating cores produced analogously to the tablets with agents that are commonly used in tablet coatings, for example polyvinyl pyrrolidone or shellac, gum arabic, talc, titanium dioxide or sugar. The shell of the coated tablet in this case can also consist of several layers, whereby, for example, the above-mentioned adjuvants are used.

Solutions or suspensions with the active ingredient according to the invention can be mixed with substances such as saccharine, cyclamate or sugar and/or with flavoring substances, such as vanilla or orange extract, to improve the taste. In addition, they can be mixed with suspending adjuvants, such as sodium carboxymethyl cellulose, or preservatives such as p-hydroxybenzoic acid.

The preparation of capsules can be carried out by mixing a pharmaceutical substance with vehicles such as lactose or sorbitol, which then are introduced into the capsules.

The production of suppositories is preferably carried out by mixing the active ingredient with suitable support materials such as neutral fats or polyethylene glycols or derivatives thereof.

A high oral bio-availability of the active ingredient is produced from the depot effect that allows, on the one hand, very low dosages of the sulfamate and, on the other hand, the application at longer intervals.

This means that the dosages for the compounds according to the invention, if they are used as a prodrug, can be very much lower in oral administration than in administration of the active ingredient itself that is contained in the prodrug, and the active ingredient can be administered at longer intervals.

For J995, it was found, for example, that the individual dosage unit can be 20–300 μg of estrogen sulfamate for an administration interval of 1 to 3 days, 0.5–5.0 mg of estrogen sulfamate for an administration interval of 5 to 10 days, or 2.0–20 mg of estrogen sulfamate for an administration interval of 20 to 40 days.

The compounds, active ingredients and spacers according to the invention are commercially available or can be produced according to the processes that are known in the literature [see, for example, S. Schwarz et al., Steroids 61 (1996) 710–717; Pharmazie [Pharmaceutics] 30 (1975) 17 ff., WO96/05216, WO97/14712, WO93/05064, DE-A-1203042, Appel, Senkpiel, Chem. Ber. 92 (1959) 1102–1104, G. Weiss, G. Schulze, Justus Liebigs Ann. Chem. 729 (1969) 40–51, M. J. Reed et al., Pharm. Sci. (1996) 11–16, U. G. Sahm et al., Pharm. Sci. (1996) 17–20].

Figure 2:
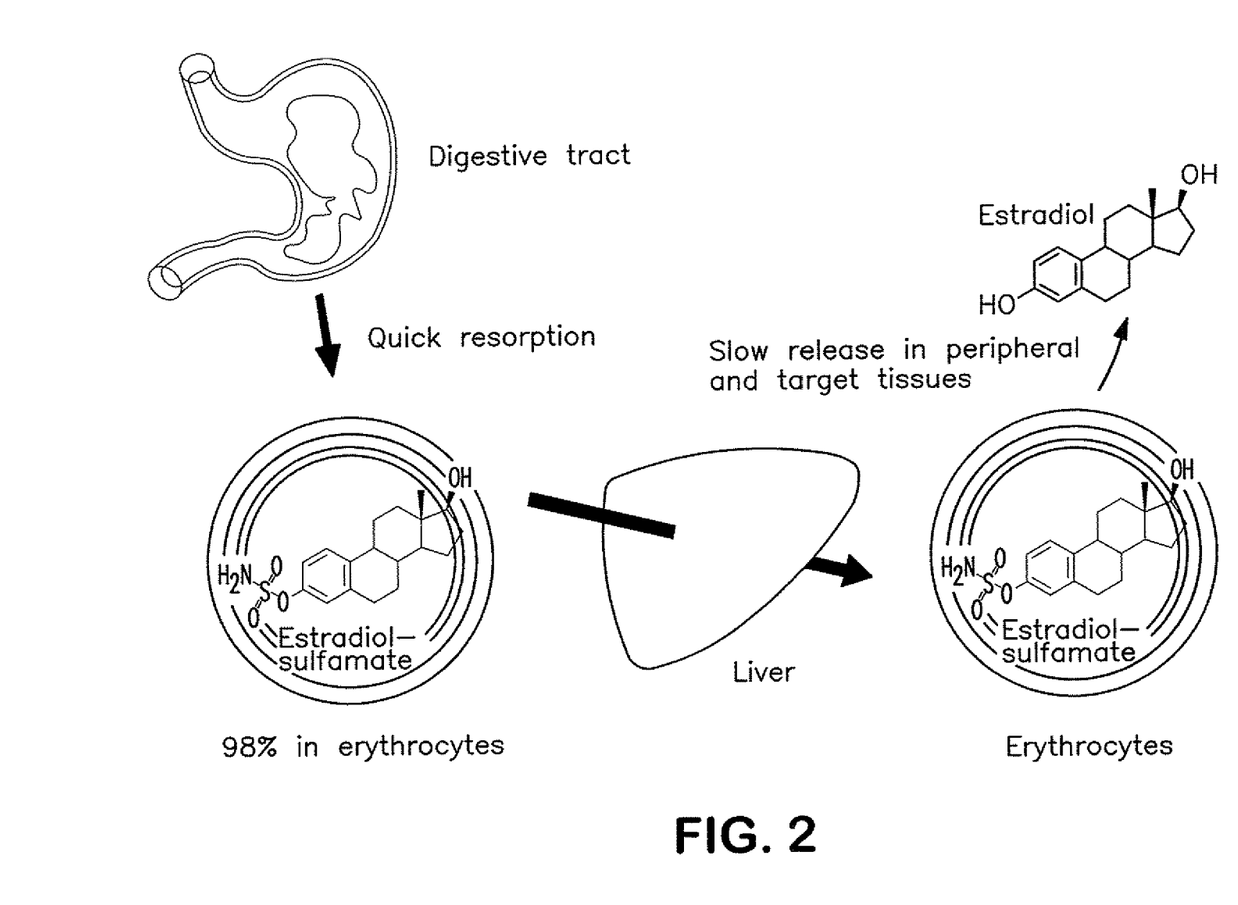
FIG. 2 explains the principle according to the invention based on J995.

Presentation of the Advantages of the Principle According to the Invention:

Estrogen sulfamates are prodrugs of estrogens and show pharmacokinetic properties that are different from the estrogens after oral administration, comparable kinetics that are achieved in the case of transdermal administration. After oral administration, estradiol sulfamate is resorbed by the gastrointestinal tract and is taken up into erythrocytes or bonded to erythrocytes. By the uptake into erythrocytes or by the binding to erythrocytes, the extraction of the sulfamate from the blood during the (first) liver passage and thus its metabolism and excretion are prevented, causing the estradiol sulfamate to show, i.a., a reduced hepatic estrogenicity. The estradiol sulfamate is enriched in the erythrocytes by a multiple (factor: 98:2) of the plasma concentration, whereby a depot of the estradiol sulfamate is produced that makes possible the slow release of the estradiol sulfamate into peripheral tissues and target tissues (see FIG. 2). This makes possible an extension of the dwell time of the estradiol sulfamate in the organism, and the occurrence of very high levels in the plasma is avoided.

Characteristic of the estradiol sulfamate are the following:
(a) Uptake of the prodrug into erythrocytes or binding of the prodrug to erythrocytes and
(b) Concentration of the prodrug in the erythrocytes by a multiple of the plasma concentration (depot effect).
(c) Slow release of the active ingredient from the depot.

The following advantages are produced therefrom:
Very uniform and prolonged active ingredient level in the blood based on the depot effect,
High oral bio-availability of the active ingredient, which on the one hand allows very low dosages of the sulfamate and, on the other hand, allows the administration at longer intervals,
Reduction of the individual variation of blood levels, as well as
Reduction of the hepatic estrogenic action.

Identification of the Specific Carrier Protein for Estradiol Sulfamate in Erythrocytes

Figure 3:
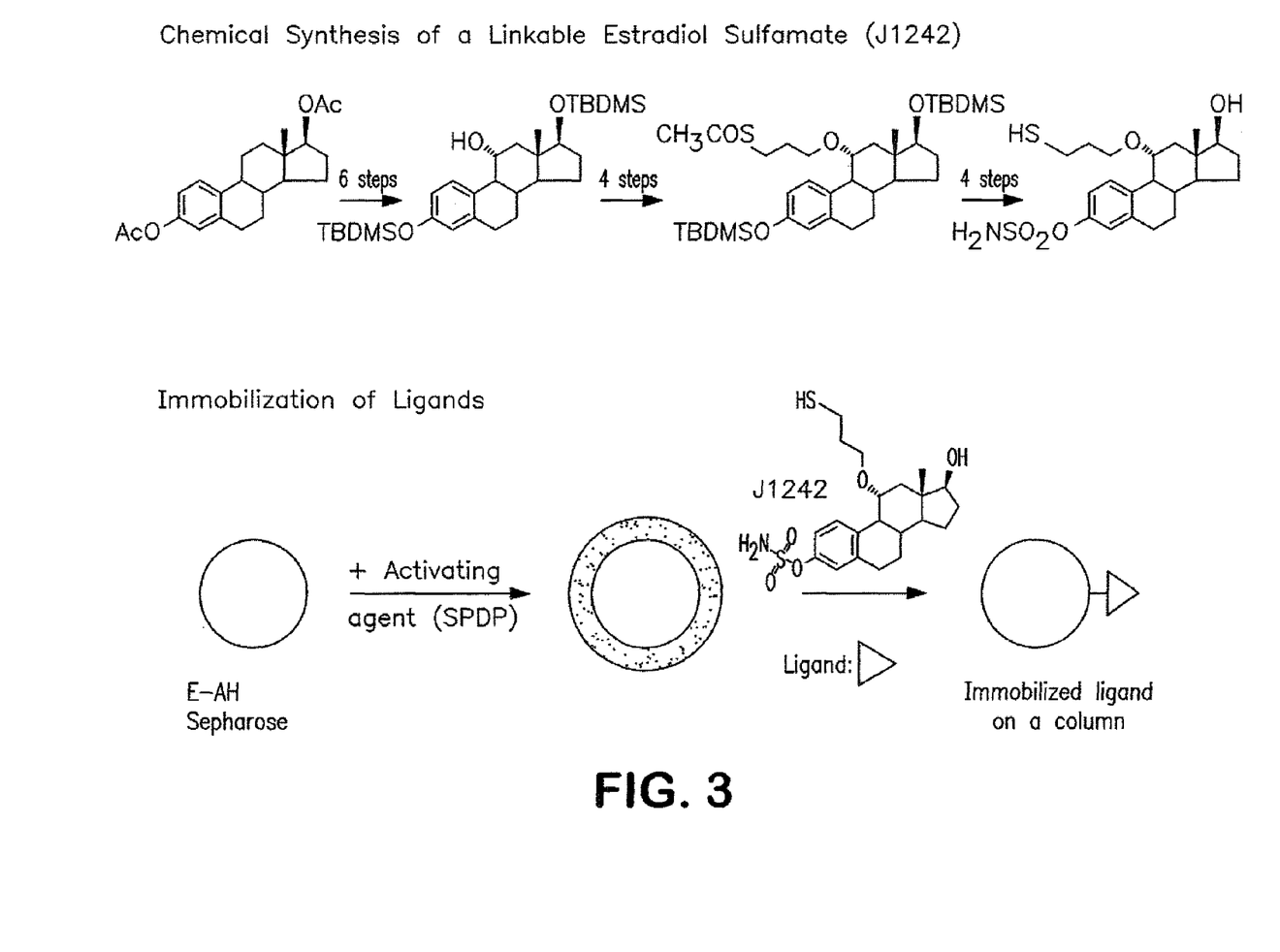
FIG. 3 shows the chemical synthesis of a linkable estradiol sulfamate (J1242) and the immobilization of this ligand.

In FIG. 3, the chemical synthesis of a linkable estradiol sulfamate (J1242) is shown, which is described in S. Schwarz et al., Steroids 64 (1999) 460–471.

After the estradiol sulfamate derivative is immobilized in the column material (E-AH-sepharose), proteins of erythrocyte-lysates were separated on the column. The protein that is responsible for the binding of estradiol sulfamate in erythrocytes was adsorbed on the surface of the affinity chromatography column. After the protein remaining on the column was washed and eluted with an acetate buffer, the eluate was analyzed with use of the "Western Plot Technique" (see FIGS. 4 and 5).

Figure 4:
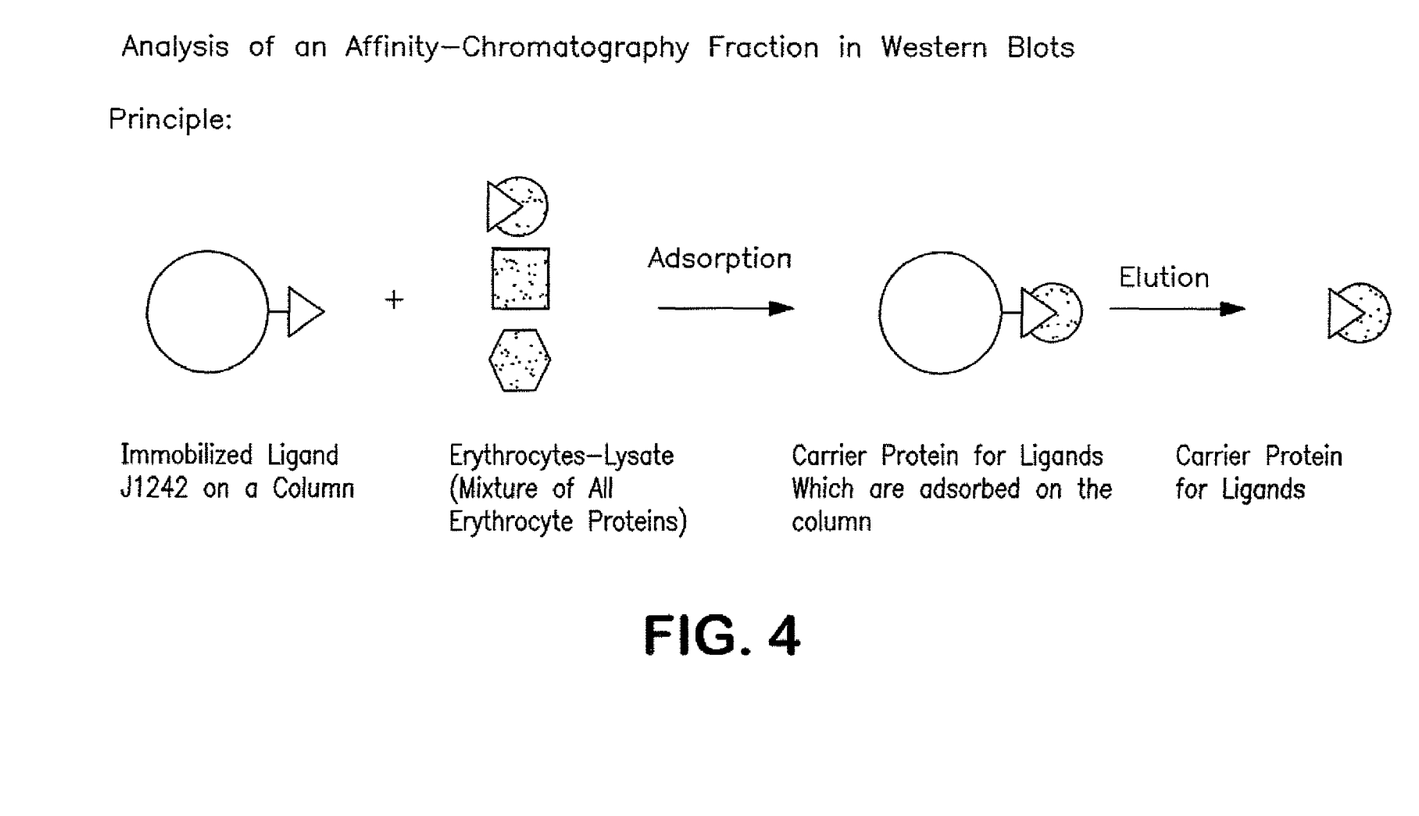
FIGS. 4 and 5 show analyses of an affinity-chromatography fraction in Western Blots.
Figure 5:
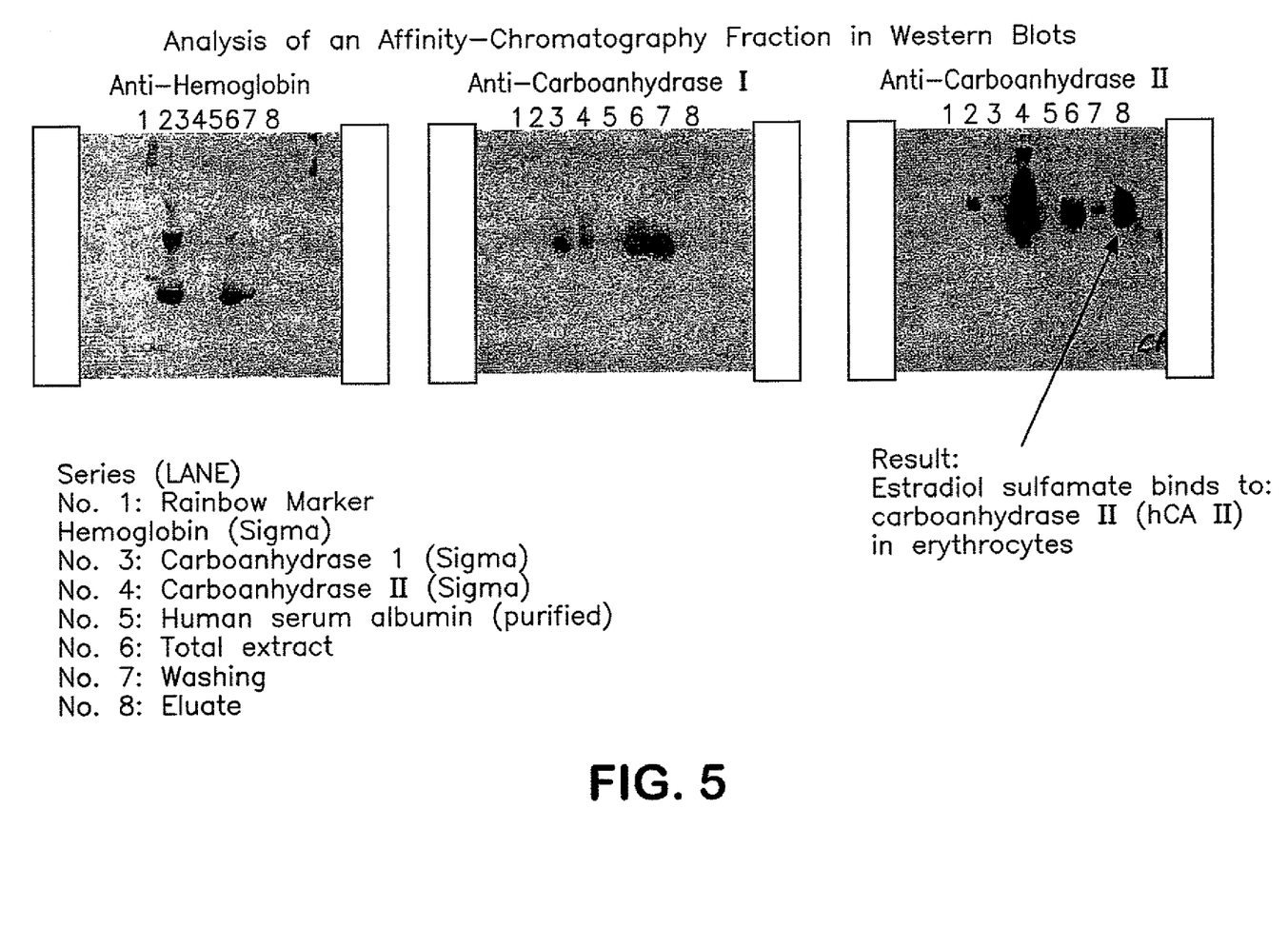

As a result, it was found that the estradiol sulfamate in erythrocytes binds to the carboanhydrase II (hCA II). The affinity chromatography shows that protein components of the erythrocytes are specifically bonded, whereby this result does not exclude the binding of estradiol sulfamate and of substances according to the invention to other proteins in erythrocytes, if the affinity of these proteins to J1242 lags behind that of hCA II.

The invention claimed is:
1. A prodrug of the following formula
Active ingredient - Spacer $SO_2NH_2$
in which - $SO_2NH_2$ enhances uptake of said active ingredient with an erythrocyte, wherein
the spacer is wherein n is a number 0 or 1 and q is a number 1, $R^5$ and $R^6$ each, independently of one another, is a hydrogen atom or an alkyl radical, and D is an arylene group, which is optionally substituted;
the active ingredient is estradiol or estriol;
the active ingredient in its free form has a 3-, 16- or 17-hydroxy functional group, which together with the spacer and with the $-SO_2NH_2$ forms a $-O$-spacer-$SO_2NH_2$ group.

2. A method of facilitating the uptake of an active ingredient into a erythrocyte and/or binding an active ingredient to a erythrocyte comprising administering to the erythrocyte a prodrug of the following formula
Active ingredient Spacer - $SO_2NH_2$
in which - $SO_2NH_2$ enhances uptake of said active ingredient with an erythrocyte,
wherein
the spacer is wherein n is a number 0 or 1 and q is a number 1, $R^5$ and $R^6$ each, independently of one another, is a hydrogen atom or an alkyl radical, and D is an arylene group, which is optionally substituted;
the active ingredient is estradiol or estriol;
the active ingredient in its free form has a 3-, 16- or 17-hydroxy functional group, which together with the spacer and with the $-SO_2NH_2$ forms a $-O$-spacer-$SO_2NH_2$ group,
wherein the uptake of the prodrug into the erythrocyte and/or the binding of the prodrug to the erythrocyte is carried out via hemoglobin, membrane protein and/or carboanhydrase.

3. A prodrug according to claim 1, wherein the active ingredient is estradiol.

4. A depot forming pharmaceutical composition comprising a prodrug according to claim 1 and a pharmaceutically acceptable carrier.

5. A prodrug according to claim 1, wherein the active ingredient is estriol.

6. A prodrug according to claim 1, wherein D is a phenylene group, a halophenylene group, a hydroxyphenylene group, a naphthylene group, pyridine, furan, thiophene, pyrrole, imidazole, pyrazine, pyrimidine or pyridazine ring.

7. A prodrug according to claim 1, wherein D is a phenylene group, a halophenylene group, a hydroxyphenylene group or a naphthylene group.

8. A prodrug according to claim 1, wherein D is a phenylene group.

9. A prodrug of the following formula
Active ingredient -Spacer-$SO_2NH_2$
in which -$SO_2NH_2$ enhances uptake of said active ingredient with an erythrocyte,
wherein
the active ingredient is estradiol or estriol, and
the spacer is wherein n is a number 0 or 1 and q is a number 1, $R^5$ and $R^6$ each, independently of one another, is a hydrogen atom or an alkyl radical, and D is an arylene group, which is optionally substituted.

10. A prodrug according to claim 9, wherein D is a phenylene group, a halophenylene group, a hydroxyphenylene group, a naphthylene group, pyridine, furan, thiophene, pyrrole, imidazole, pyrazine, pyrimidine or pyridazine ring.

11. A prodrug according to claim 9, wherein D is a phenylene group, a halophenylene group, a hydroxyphenylene group or a naphthylene group.

12. A prodrug according to claim 9, wherein D is a phenylene group.

13. A method according to claim 2, wherein the active ingredient is estradiol.

14. A method according to claim 2, wherein the active ingredient is estriol.

15. A method according to claim 2, wherein D is a phenylene group, a halophenylene group, a hydroxyphenylene group, a naphthylene group, pyridine, furan, thiophene, pyrrole, imidazole, pyrazine, pyrimidine or pyridazine ring.

16. A method according to claim 2, wherein D is a phenylene group, a halophenylene group, a hydroxyphenylene group or a naphthylene group.

17. A method according to claim 2, wherein D is a phenylene group.

18. A prodrug according to claim 1, wherein D is an arylene group, which is not substituted.

* * * * *

UNITED STATES PATENT AND TRADEMARK OFFICE
CERTIFICATE OF CORRECTION

PATENT NO. : 7,507,725 B2 Page 1 of 1
APPLICATION NO. : 10/296973
DATED : March 24, 2009
INVENTOR(S) : Elger et al.

It is certified that error appears in the above-identified patent and that said Letters Patent is hereby corrected as shown below:

Column 10, line 65 reads "Active ingredient - Spacer $SO_2NH_2$" should read
-- Active ingredient - Spacer - $SO_2NH_2$ --

Column 11, line 24 reads "Active ingredient Spacer - $SO_2NH_2$" should read
-- Active ingredient - Spacer - $SO_2NH_2$ --

Signed and Sealed this

Twelfth Day of October, 2010

David J. Kappos
*Director of the United States Patent and Trademark Office*